(12) United States Patent
Kaczvinsky, Jr. et al.

(10) Patent No.: US 7,101,889 B2
(45) Date of Patent: *Sep. 5, 2006

(54) LIPASE INHIBITING COMPOSITION

(75) Inventors: Joseph Robert Kaczvinsky, Jr., Cincinnati, OH (US); Charles Raymond Degenhardt, Cincinnati, OH (US); Garry Steven Garrett, Fairfield, OH (US); Charles Winston Saunders, Fairfield, OH (US); David Joseph Eickhoff, Edgewood, KY (US); Celeste Dawn Gale, Hamilton, OH (US); Nancy Lynn Reeder, Cincinnati, OH (US)

(73) Assignee: The Procter & Gamble, Cincinnati, OH (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/368,931

(22) Filed: Feb. 19, 2003

(65) Prior Publication Data

US 2003/0165449 A1    Sep. 4, 2003

Related U.S. Application Data

(60) Provisional application No. 60/357,800, filed on Feb. 19, 2002, provisional application No. 60/358,196, filed on Feb. 20, 2002.

(51) Int. Cl.
 *A61K 31/435*   (2006.01)
 *A61K 31/15*    (2006.01)
(52) U.S. Cl. ..................... 514/277; 514/640
(58) Field of Classification Search ............... None
 See application file for complete search history.

(56) References Cited

U.S. PATENT DOCUMENTS 3,091,241 A    5/1963    Kellett 3,961,486 A    6/1976    Granholm et al.

FOREIGN PATENT DOCUMENTS

| DE | 199 21 794 A1 | 11/2000 |
| EP | 0 117 632 | 8/1989 |
| EP | 1 048 288 A1 | 2/2000 |
| WO | WO 95/01155 | 1/1995 |
| WO | WO 95/24896 | 9/1995 |
| WO | WO 97/06770 | 2/1997 |
| WO | WO 99/45973 | 9/1999 |
| WO | WO 99/48471 | 9/1999 |

OTHER PUBLICATIONS

George Kokotos, Robert Verger, and Antonia Chiou; "Synthesis of 2-Oxo Amide Triacylglycerol Analogues and Study of Their Inhibition Effect on Pancreatic and Gastric Lipases"; *Chem. Eur. J.*; pp. 4211-4217; vol. 6 No. 22; Wiley-VCH Verlag GmbH, D-69451 Weinheim, 2000.
A.K. Gupta, Y. Kohli, A.Li, J. Faergemann, and R.C. Summberbell; "In vitro susceptibility of the severn Malassezia species to ketoconazole, voriconazole, itraconazole and terbinafine"; *British Journal of Dermatology* 2000 vol. 142 pp. 758-765; 2000 Britich Association of Dermatologists.
James G. Weeks, PH.D.; Leslie McCarty, PH.D.; Thomas Black, B.S.; & James E. Fulton, Jr., M.D., Ph.D.; "The Inability of a Bacterial Lipase Inhibitor to Control Acne Vulgaris", *The Journal of Investigative Dermatology*; Aug. 1977; vol. 69 Issue 2; The Williams & Wilkins Company in the United States.

*Primary Examiner*—Jean C. Witz
(74) *Attorney, Agent, or Firm*—Melody A. James; Brent M. Peebles

(57) ABSTRACT

The invention relates to compositions for treating dandruff comprising compounds that are non-polymeric and/or have a weight average molecular weight of less than about 1000. These compounds, when used at a concentration of about 0.001% or less, inhibit the activity of any *Malassezia globosa* lipase by at least 50%. The invention also relates to the use of these compounds for inhibiting lipase activity.

8 Claims, No Drawings

LIPASE INHIBITING COMPOSITION

CROSS REFERENCE TO RELATED APPLICATION

The application claims the benefit of U.S. Provisional application Ser. No. 60/357,800, filed on Feb. 19, 2002, and U.S. Provisional application Ser. No. 60/358,196, filed on Feb. 20, 2002 in the names of Kaczvinsky et al.

FIELD

The invention relates to low molecular weight compounds, non-polymeric compounds and compositions containing these compounds which inhibit lipase enzymes or reduce the lipase enzyme activity.

BACKGROUND

Various types of lipase enzymes are present on our skin, including enzymes from micro-organisms, enzymes derived from our diet and enzymes produced by the body. It is known that some of these enzymes can have undesirable effects. For example, enzymes are believed to cause skin rashes and possibly infections of the body. This problem is encountered by the users of articles which are in contact with the skin (and the lipase enzymes thereon), such as bandages, plaster, diapers, incontinence articles, sanitary towels, training pants etc. It is also believed that the some of these enzymes can be responsible for the development of dandruff.

Manufacturers of skin and health care products have developed products over the past decades which help reduce the occurrence of problems caused by enzymes, in particular skin rash. The main focus of these products has been to reduce the exposure of the skin to the enzymes.

There is evidence in the literature of skin disease linked to lipase enzymes created by microorganisms on the skin. These skin diseases include acne and dandruff. The lipase enzymes create fatty acids from triglycerides. The fatty acids are somehow related to the etiology of the diseases. One approach to relieving the condition is to block the activity of the lipase enzymes.

Various lipase enzyme inhibitors are known in the art. For example, antibodies which are specific to certain lipase enzymes are used, such as described in WO 95/24896 and WO 95/01155. EP 0117632-B relates to disposable articles which comprise lipase inhibiting agents, preferably zinc containing components, and a vehicle material. U.S. Pat. No. 3,091,241 relates to the use of triacetin in tampons to inhibit lipase enzyme activity. U.S. Pat. No. 3,961,486 teaches the use of adipic acid to reduce the lipase enzyme activity and to reduce the skin rash. Also, WO 99/48471 discloses certain copolymeric lipase inhibitors.

However, none of the above-mentioned inhibitors have been shown to be particularly effective at treating dandruff in shampoo applications. Dandruff is believed to be caused and/or exacerbated by the presence of fungus on the scalp and the products generated by the lipase enzymes created by the fungus. Therefore, a need still exists for compounds directed towards inhibiting dandruff-causing lipase enzymes.

SUMMARY

The inventors have found that a particular fungus, *Malassezia globosa*, can be linked to the creation of dandruff. *Malassezia globosa* is commonly found on human scalps. In addition, the inventors have now found that particular low molecular weight and/or non-polymeric compounds, can effectively inhibit *Malassezia globosa* lipase enzymes, or reduce the *Malassezia globosa* lipolytic enzyme activity. The compounds have been found to be useful in reducing dandruff and in various other applications where reduction of the *Malassezia globosa* lipolytic enzyme activity is desired. It has been found that the compounds or compositions containing the compound are capable of reducing or preventing dandruff; it has also been found that the compositions or compounds can improve the longevity of a perfume, e.g. protect the perfume esters from degradation by the enzymes; it has also been found that the compositions or compounds can improve the preservation of food and beverage products; it has also been found that the compositions or compounds can improve the healing of wounds.

The present invention is directed to a composition for treating dandruff comprising a compound having a weight average molecular weight of less than about 1000; wherein the compound, when used at a concentration of about 0.001% or less, inhibits the activity of any *Malassezia globosa* lipase by at least 50%, as indicated by glycerol production, using the following method:

a) Add 270 µl of 25 mM MES, pH 5.5, 90 mM NaCl, 8 mM KCl, and 1 mM $CaCl_2$ to each well of a deep well 96-well plate;
b) Add 10 µl of olive oil, diluted three-fold into dimethyl sulfoxide, to each well;
c) Add 15 µl of a candidate inhibitor compound to each well;
d) Add 5 µl of *Malassezia globosa* lipase polypeptide to each well;
e) Cover the 96-well plate;
f) Vigorously shake the 96-well plate for one hour at room temperature;
g) Following the one-hour period, spin the 96-well plate briefly in a centrifuge to force the liquid into the bottom of the well;
h) After spinning, raise the pH in each well by adding 50 µl of 1 M Tris HCl pH 8.0;
i) Transfer 90 µl of the solution in each well to a standard microtiter plate;
j) Prepare a glycerol detection solution by combining 100 mM Tris HCl pH 7.6, 10 mM $MgCl_2$, 2 mM 4-aminoantipyrine, 3 mM N-ethyl-N-(3-sulfopropyl)-m anisidine, 1 mM adenosine 5'-triphosphate, 20 units/ml peroxidase, 8 units/ml glycerol-3-phosphate oxidase, and 0.5 units/ml glycerol kinase;
k) Add 90 µl of said glycerol detection solution to each well of the standard microtiter plate;
l) Rotate the standard microtiter plate on a lab rotator for 15 minutes at room temperature;
m) Measure the optical density at 540 nm, this is as an indication of the amount of glycerol produced;
n) Generate a standard curve with known glycerol concentrations to know the absolute amount of glycerol generated;
o) Compare the level of glycerol produced in step "m" to the standard curve.

The present invention is further directed to a composition for treating dandruff comprising a non-polymeric compound; wherein the compound, when used at a concentration of about 0.001% or less, inhibits the activity of any *Malassezia globosa* lipase by at least 50%, as indicated by glycerol production, using the following method:

The present invention is further directed to a method of using the compositions.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The low molecular weight and/or non-polymeric compounds of the invention, as described herein, reduce the enzyme activity of *Malassezia globosa* lipase enzymes, by inactivating the enzymes. Thus, the invention is concerned with the use of the compounds described hereinafter, for preparation of compositions to inhibit or reduce the enzyme activity of *Malassezia globosa* lipase enzyme activity.

The general activity of lipase enzymes is to hydrolyse fats present in the ester form (such as the glycerides found in human skin), and accordingly generate fatty acids and glycerol, which can be a source of energy for the fungus but also can cause irritation, dandruff and body odor. The inventors have found that the lipase enzymes produced by the *Malassezia globosa* fungus are particularly problematic in creating dandruff.

The lipase inhibiting compounds of the present invention can be used in any application where reduction of the enzyme activity of the *Malassezia globosa* enzymes is required. In particular, the compositions are used for reduction of the enzyme activity of lipase enzymes in contact with the human or animal body, in particular the skin or hair, such as for dandruff prevention. The compounds of the prent invention can also be used to reduce enzyme activity in food products and beverages, or to reduce enzyme activity of micro-organisms present on fabrics and surfaces, such as in kitchens and bathrooms. Thus, the compositions or the compounds of the invention are useful in personal-care products, food and beverage products and cleaning products.

The compositions of the present invention can also be used in shampoos, hair conditioners, hair styling products, eye-care products such as eye drops, antiseptic compositions, perfume compositions, tooth care products, and the compositions can be used in absorbent articles. The compounds may also be used to inhibit active lipase enzymes which remain on the fabric or in the washing water after the washing or cleaning process.

The compounds or compositions of the invention may also be useful for reduction of the enzyme activity of digestive lipolytic enzymes. Thus, the compounds may be used to treat obesity.

The compounds or compositions of the present invention can be used to treat various problems caused by lipase enzymes, including dandruff, skin rash, acne, and body odor. The compounds or compositions can also be used for preservation of food or beverage products, to increase the life of a perfume, e.g. the longevity of a perfume by reducing the degradation of the perfume esters by the lipase enzymes, and also to improve wound healing and reduce eye irritation.

By treatment is meant herein an improvement of the affected human or animal body, caused by the enzyme activity. Thus includes in one preferred aspect of the invention, the reduction or at least stabilisation of the dandruff, the skin rash or dermatitis, the acne or the body odor which is caused by enzymes.

The amount of the compounds of the invention or the compositions for the reduction of the lipase enzyme activity or in the treatment, will vary with the particular location of the condition being treated, the severity of the condition being treated, the expected duration of the treatment, any specific sensitivity to either the composition specific to the user, the condition of the user, concurrent therapies being administered, other conditions present in the user.

In preferred embodiments of the invention, it is preferred that a minimum inhibitory concentration of the compounds of the invention or the compositions thereof is used, in an amount and form such that it is available to inhibit the activity of the lipase enzymes, for example topically applied to the skin or hair, eyes or teeth, or orally taken by the user, or applied on surfaces or fabrics.

The compounds of the invention may be comprised in compositions, which may be cosmetic compositions, preferably in the form of a hair treatment composition, shampoo, conditioner, spray, cream, foam, lotion, gel, oil, ointment or powder or tablet.

Preferably, the compounds of the present invention are comprised in a shampoo, conditioner, scalp treatment, and hair styling product. In addition, the compounds of the present invention can be used in perfume compositions, cleaning compositions, eye-care compositions, and deodorant or absorbent articles, such as diapers, tissues, and wet wipes.

The compositions may comprise additional ingredients and the exact nature and levels of the additional ingredients will depend on the application of the compounds of the invention or the compositions thereof. For example, anti-dandruff agents may be a useful additional component in a shampoo comprising compounds of the present invention. Other preferred additional components of the compositions of the invention may be bactericidal or fungicidal agents and/or other enzyme inhibitors. Anti-bodies against enzymes may be present, but because of the nature of the low molecular weight and/or non-polymeric compounds in accord with the invention, they may be omitted from the compositions. In a number of applications, surfactants may be included, and in skin-care products zinc-containing compounds may be used.

*Malassezia globosa* Lipase Inhibiting Compounds

In one embodiment, the *Malassezia globosa* lipase inhibiting compounds of the present invention comprise compounds have a weight average molecular weight of less than about 1000, and the compounds, when used at a concentration of about 0.001% or less (by weight percent of the composition), inhibit the activity of any *Malassezia globosa* lipase by at least 50%. Preferably, the compounds of the present invention have a weight average molecular weight of less than about 900. More preferably, they have a weight average molecular weight of less than about 850. Still more preferably, they have a weight average molecular weight of less than about 800.

Preferably, the compounds inhibit the activity of any *Malassezia globosa* lipase by at least 50% when used at a concentration of about 0.01% or less. More preferably, the compounds inhibit the activity of any *Malassezia globosa* lipase by at least 50% when used at a concentration of about 0.001% or less. Even more preferably, the compounds inhibit the activity of any *Malassezia globosa* lipase by at least 50% when used at a concentration of about 0.0002% or less. Still more preferably, the compounds inhibit the activity of any *Malassezia globosa* lipase by at least 50% when used at a concentration of about 0.0001% or less.

In a second embodiment, the *Malassezia globosa* lipase inhibiting compounds of the present invention comprise non-polymeric compounds, and the compounds, when used at a concentration of about 0.001% or less, inhibit the activity of any *Malassezia globosa* lipase by at least 50%. The term "non-polymeric" means that the compounds do not have identical repeating sections of monomers.

Typically, glycerol production is used as an indication of lipase activity. A useful method for determining the effect of a test compound on inhibiting glycerol production of a *Malassezia globosa* lipase is as follows:

a) Add 270 µl of 25 mM MES, pH 5.5, 90 mM NaCl, 8 mM KCl, and 1 mM $CaCl_2$ to each well of a deep well 96-well plate;
b) Add 10 µl of olive oil, diluted three-fold into dimethyl sulfoxide, to each well;
c) Add 15 µl of a candidate inhibitor compound to each well;
d) Add 5 µl of *Malassezia globosa* lipase polypeptide to each well;
e) Cover the 96-well plate;
f) Vigorously shake the 96-well plate for one hour at room temperature;
g) Following the one-hour period, spin the 96-well plate briefly in a centrifuge to force the liquid into the bottom of the well;
h) After spinning, raise the pH in each well by adding 50 µl of 1 M Tris HCl pH 8.0;
i) Transfer 90 µl of the solution in each well to a standard microtiter plate;
j) Prepare a glycerol detection solution by combining 100 mM Tris HCl pH 7.6, 10 mM $MgCl_2$, 2 mM 4-aminoantipyrine, 3 mM N-ethyl-N-(3-sulfopropyl)-m anisidine, 1 mM adenosine 5'-triphosphate, 20 units/ml peroxidase, 8 units/ml glycerol-3-phosphate oxidase, and 0.5 units/ml glycerol kinase;
k) Add 90 µl of said glycerol detection solution to each well of the standard microtiter plate;
l) Rotate the standard microtiter plate on a lab rotator for 15 minutes at room temperature;
m) Measure the optical density at 540 nm, this is as an indication of the amount of glycerol produced;
n) Generate a standard curve with known glycerol concentrations to know the absolute amount of glycerol generated;
o) Compare the level of glycerol produced in step "m" to the standard curve.

Specific examples of useful compounds according to the present invention include fospirate (O,O-dimethyl-O-3,5,6-trichloro-2-pyridyl phosphate), 1,6-bis(cyclohexyloximinocarbonylamino)hexane, and the following α-keto amides:

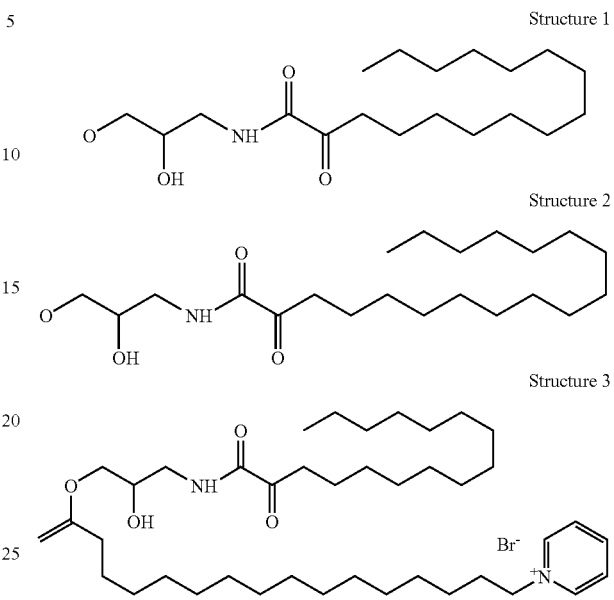

In finished compositions as described herein, in particular hair-care products, cosmetic products including skin-care products, deodorants, perfumes, cleaning products, food products, beverages and antiseptic products, the level of the compounds herein is preferably from 0.0001% to 10%, more preferably from 0.0001% to 5%, and even more preferably from 0.0001% to 1% by weight of the composition.

Method of Preparation

The compositions herein can be prepared by any method known in the art for preparation for cosmetic compositions or medicament. The exact method will depend on the nature of the composition. The compounds of the present invention can be added to the compositions separately, or for example be combined with other ingredients commonly used in cosmetic compositions or medicaments, or for example dispersed or dissolved in water or oil or a water-in-oil emulsion prior to addition to the composition.

Method of Use

The compositions of the invention can be in the form of hair-care products (shampoo, conditioner, etc.), cleaning compositions or food or beverage products. The compositions may be used directly for the relevant purpose or may be added to other products or compositions.

Preferably, the compositions of the present invention are used in a shampoo. The method of use comprises applying an effective amount of the composition to hair or skin that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing the hair and skin comprises the steps of: a) wetting the hair and/or skin with water, b) applying an effective amount of the shampoo composition to the hair and/or skin, and c) rinsing the composition from the hair and/or skin using water. These steps can be repeated as many times as desired to achieve the desired cleansing and dandruff treating benefit.

The compositions can also be in the form of personal-care compositions or products. Then, the composition of the invention can be administered to the user by any method known in the art, depending on the application of the composition and the purpose of use. It may be preferred that the composition is applied to the skin or hair, which will be in contact with, or the vicinity of the lipase enzymes. It may be preferred that the composition is administered orally to the user.

When the composition is used for treatment of body odor, the composition may preferably be in the form of a deodorant composition, in the form of a fluid, gel, cream or powder, contained in a stick or spray.

When the composition is used for treatment of dermatitis, acne or skin rash, the composition may preferably be in the form of cream or lotion or aftershave, preferably comprising an alcohol, preferably a mixture of ethanol in water, and preferably also comprising a perfume component.

The compositions can also be initially applied to an article, which will then be applied to the skin.

The compositions of the present invention may also be comprised in an absorbent article, preferably a disposable absorbent article. As used herein, the term "absorbent articles" refers to devices which absorb and contain body exudates or blood, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). The structure of the disposable absorbent article is not critical to the practice of the present invention. Preferred articles are bandages, plaster, wipes, catamenials and diapers, or also tissue and tampons.

Additional Ingredients

The composition of the invention can comprise additional ingredients. Which ingredients are present and at which level depends on the character of the composition and the use thereof. Highly preferred ingredients are surfactants.

Detersive surfactants are particularly useful in cleaning compositions such as shampoos. Preferably, the compositions of the present invention include a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the compositions are the alkyl. and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the compositions of the present invention include sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R^1—SO_3\text{-M}]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic detersive surfactants suitable for use in the compositions are the succinates, examples of which include disodium N-octadecylsulfosuccinnate; disodium lauryl sulfosuccinate; diammonium lauryl sulfosuccinate;

tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are monoolefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the compositions are the beta-alkyloxy alkane sulfonates. These surfactants conform to the formula

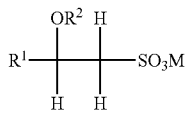

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. Nos. 5,104,646 (Bolich Jr. et al.), 5,106,609 (Bolich Jr. et al.), which descriptions are incorporated herein by reference.

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition of the present invention are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable optional surfactants include nonionic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which descriptions are incorporated herein by reference.

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Aqueous Carrier

The compositions of the present invention are typically in the form of pourable liquids (under ambient conditions). The compositions will therefore typically comprise an aqueous carrier, which is present at a level of from about 20% to about 95%, preferably from about 60% to about 85%, by weight of the compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Cationic Polymers

The compositions of the present invention may contain an organic cationic polymer. Concentrations of the cationic polymer in the composition typically range from about 0.05% to about 3%, preferably from about 0.075% to about 2.0%, more preferably from about 0.1% to about 1.0%, by weight of the composition. Preferred cationic polymers will have cationic charge densities of at least about 0.9 meq/gm, preferably at least about 1.2 meq/gm, more preferably at least about 1.5 meq/gm, but also preferably less than about 7 meq/gm, more preferably less than about 5 meq/gm, at the pH of intended use of the composition, which pH will generally range from about pH 3 to about pH 9, preferably between about pH 4 and about pH 8. The "cationic charge density" of a polymer, as that term is used herein, refers to the ratio of the number of positive charges on a monomeric unit of which the polymer is comprised to the molecular weight of said monomeric unit. The cationic charge density multiplied by the polymer molecular weight determines the number of positively charged sites on a given polymer chain. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be use in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370 and FC 905); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer, copolymers of acrylamide and dimethyidiallylammonium chloride (referred to in the industry by CTFA as Polyquaternium 6 and Polyquaternium 7, respectively), such as those available under the MERQUAT tradename as Merquat 100 and Merquat 550 from Calgon Corp. (Pittsburgh, Pa., USA); amphoteric copolymers of acrylic acid including copolymers of acrylic acid and dimethyldiallylammonium chloride (referred to in the industry by CTFA as Polyquaternium 22) such as those available from Calgon Corp. under the Merquat tradename (e.g. Merquat 280 and 295), terpolymers of acrylic acid with dimethyldiallylammonium chloride and acrylamide (referred to in the industry by CTFA as Polyquaternium 39) such as those available from Calgon Corp. under the Merquat tradename (e.g. Merquat 3300 and 3331), and terpolymers of acrylic acid with methacrylamidopropyl trimethylammonium chloride and methylacrylate (referred to in the industry by CTFA as Polyquaternium 47)

available from Calgon Corp. under the Merquat tradename (e.g. Merquat 2001). Preferred cationic substituted monomers are the cationic substituted dialkylaminoalkyl acrylamides, dialkylaminoalkyl methacrylamides, and combinations thereof. These preferred monomers conform the to the formula

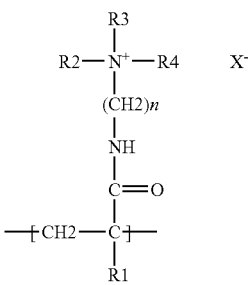

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

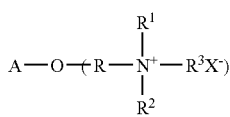

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially avaialable from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference. When used, the cationic polymers herein are either soluble in the composition or are soluble in a complex coacervate phase in the composition formed by the cationic polymer and the anionic detersive surfactant component described hereinbefore. Complex coacervates of the cationic polymer can also be formed with other charged materials in the composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49–54, C. J. van Oss, "Coacervation, Complex-Coacervation and Flocculation", J. Dispersion Science and Technology, Vol. 9 (5,6), 1988–89, pp 561–573, and D. J. Burgess, "Practical Analysis of Complex Coacervate Systems", J. of Colloid and Interface Science, Vol. 140, No. 1, November 1990, pp 227–238, which descriptions are incorporated herein by reference.

It is believed to be particularly advantageous for the cationic polymer to be present in the composition in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo composition as a coacervate phase or form a coacervate phase upon dilution.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

Conditioning Agents

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the compositions of the present invention typically comprise a water insoluble, water dispersible,r non-volatile, liquid that forms emulsified, liquid particles or are solubilized by the surfactant micelles, in the anionic detersive surfactant component (described herein). Suitable conditioning agents for use in the composition are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, most preferably from about 0.2% to about 3%. Non-limiting examples of suitable silicone conditioning-agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, most preferably from about 100,000 to about 1,500,000 csk.

The dispersed, silicone conditioning agent particles typically have a number average particle diameter ranging from about 0.01 μm to about 50 μm. For small particle application to hair, the number average particle diameters typically range from about 0.01 μm to about 41 μm, preferably from about 0.01 μm to about 2 μm, more preferably from about 0.01 μm to about 0.5 μm. For larger particle application to hair, the number average particle diameters typically range from about 4 μm to about 50 μm, preferably from about 6 μm to about 30 μm, more preferably from about 9 μm to about 20 μm, most preferably from about 12 μm to about 18 μm. Conditioning agents having an average particle size of less than about 5μm may deposit more efficiently on the hair. It is believed that small size particles of conditioning agent are contained within the coacervate that is formed between the anionic surfactant component (described herein) and the cationic polymer component (described herein), upon dilution of the shampoo.

Background material on silicones including sections discussing silicone fluids, gums, and resins, as well as manufacture of silicones, are found in *Encyclopedia of Polymer Science and Engineering*, vol. 15, 2d ed., pp 204–308, John Wiley & Sons, Inc. (1989), incorporated herein by reference.

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 10 csk to about 100,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids, having hair conditioning properties may also be used.

Silicone oils include polyalkyl or polyaryl siloxanes which conform to the following Formula (III):

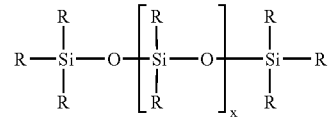

wherein R is aliphatic, preferably alkyl or alkenyl, or aryl, R can be substituted or unsubstituted, and x is an integer from 1 to about 8,000. Suitable unsubstituted R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the compositions, are chemically stable under normal use and storage conditions, are insoluble in the compositions herein, and are capable of being deposited on and conditioning the hair. The two R groups on the silicon atom of each monomeric silicone unit may represent the same or different groups. Preferably, the two R groups represent the same group.

Preferred alkyl and alkenyl substituents are $C_1$ to $C_5$ alkyls and alkenyls, more preferably from $C_1$ to $C_4$, most preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, most preferably from $C_1$ to $C_2$. As discussed above, the R substituents can also contain amino functionalities (e.g. alkamino groups), which can be primary, secondary or tertiary amines or quaternary ammonium. These include mono-, di- and tri- alkylamino and alkoxyamino groups, wherein the aliphatic portion chain length is preferably as described herein. The R substituents may also be substituted with other groups, such as halogens (e.g. chloride, fluoride, and bromide), halogenated aliphatic or aryl groups, hydroxy (e.g.

hydroxy substituted aliphatic groups), and mixtures thereof. Suitable halogenated R groups could include, for example, tri-halogenated (preferably tri-fluoro) alkyl groups such as —$R^1CF_3$, wherein $R^1$ is a $C_1$–$C_3$ alkyl. An example of such a polysiloxane includes, but is not limited to, polymethyl 3,3,3-trifluoropropylsiloxane.

Suitable R groups for use in the compositions of the present invention include, but are not limited to: methyl, ethyl, propyl, phenyl, methylphenyl and phenylmethyl. Specific non-limiting examples of preferred silicones include: polydimethyl siloxane, polydiethylsiloxane, and polymethylphenylsiloxane. Polydimethylsiloxane is especially preferred. Other suitable R groups include: methyl, methoxy, ethoxy, propoxy, and aryloxy. The three R groups on the end caps of the silicone may represent the same or different groups.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition described herein.

Alkylamino substituted silicones suitable for use in the compositions of the present invention include, but are not limited to, those which conform to the following general Formula (IV):

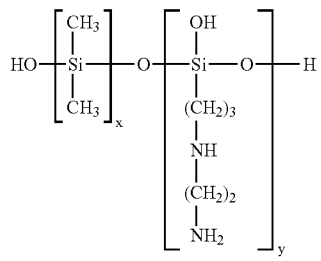

wherein x and y are integers. This polymer is also known as "amodimethicone."

b. Cationic Silicones

Cationic silicone fluids suitable for use in the compositions of the present invention include, but are not limited to, those which conform to the general formula (V):

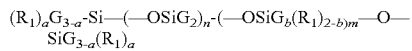

wherein G is hydrogen, phenyl, hydroxy, or $C_1$–$C_8$ alkyl, preferably methyl; a is 0 or an integer having a value from 1 to 3, preferably 0; b is 0 or 1, preferably 1; n is a number from 0 to 1,999, preferably from 49 to 149; m is an integer from 1 to 2,000, preferably from 1 to 10; the sum of n and m is a number from 1 to 2,000, preferably from 50 to 150; $R_1$ is a monovalent radical conforming to the general formula $C_qH_{2q}L$, wherein q is an integer having a value from 2 to 8 and L is selected from the following groups:

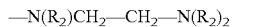

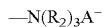

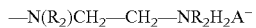

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (V) is the polymer known as "trimethylsilylamodimethicone", which is shown below in formula (VI):

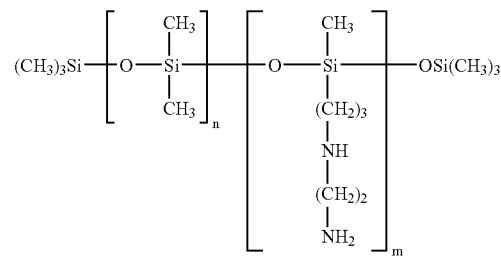

Other silicone cationic polymers which may be used in the compositions of the present invention are represented by the general formula (VII):

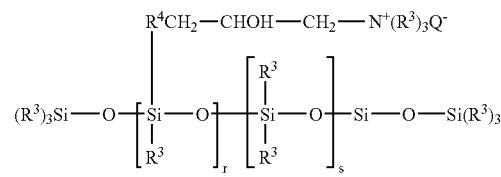

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, all of which are incorporated herein by reference. The silicone gums will typically have a weight average molecular weight in excess of about 200,000, preferably from about 200,000 to about 1,000,000. Specific non-limiting examples of silicone gums for use in the compositions of the present invention include polydimethylsiloxane, (polydimethylsiloxane) (methylvinylsiloxane) copolymer, poly(dimethylsiloxane) (di-phenyl siloxane)(methylvinylsiloxane) copolymer and mixtures thereof.

d. High refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

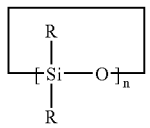

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted. Substituents include aliphatic substituents, and may also include alkoxy substituents, acyl substituents, ketones, halogens (e.g., Cl and Br), amines, and the like. Examples of aryl-containing groups include, but are not limited to, substituted and unsubstituted arenes, such as phenyl, and phenyl derivatives, such as phenyls with $C_1$–$C_5$ alkyl or alkenyl substituents. Specific non-limiting examples include: allylphenyl, methyl phenyl and ethyl phenyl, vinyl phenyls (e.g. styrenyl), and phenyl alkynes (e.g. phenyl $C_2$–$C_4$ alkynes). Heterocyclic aryl groups include, but are not limited to, substituents derived from furan, imidazole, pyrrole, pyridine, and the like. Examples of fused aryl ring substituents include, but are not limited to, napthalene, coumarin, and purine.

Generally, the high refractive index polysiloxane fluids will have a degree of aryl-containing substituents of at least about 15%, preferably at least about 20%, more preferably at least about 25%, even more preferably at least about 35%, most preferably at least about 50%. Typically, the degree of aryl substitution will be less than about 90%, more generally less than about 85%, preferably from about 55% to about 80%.

The high refractive index polysiloxane fluids are also characterized by relatively high surface tensions as a result of their aryl substitution. Generally, the polysiloxane fluids will have a surface tension of at least about 24 dynes/cm², typically at least about 27 dynes/cm². Surface tension, for purposes hereof, is measured by a de Nouy ring tensiometer according to Dow Corning Corporate Test Method CTM 0461 (23 November, 1971). Changes in surface tension can be measured according to the above test method or according to ASTM Method D 1331.

Preferred high refractive index polysiloxane fluids have a combination of phenyl or phenyl derivative substituents (most preferably phenyl), with alkyl substituents, preferably $C_1$–$C_4$ alkyl, (most preferably methyl), hydroxy, or $C_1$–$C_4$ alkylamino (especially —$R^1NHR^2NH2$ wherein each $R^1$ and $R^2$ independently is a $C_1$–$C_3$ alkyl, alkenyl, and/or alkoxy). High refractive index polysiloxanes are available from Dow Corning, Huls America, and General Electric.

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair.

Also, the spreading agent will preferably reduce the surface tension by at least about 2 dynes/cm², preferably at least about 3 dynes/cm², even more preferably at least about 4 dynes/cm², most preferably at least about 5 dynes/cm².

The surface tension of the mixture of the polysiloxane fluid and the spreading agent, at the proportions present in the final product, is preferably less than or equal to about 30 dynes/cm², more preferably less than or equal to about 28 dynes/cm², most preferably less than or equal to about 25 dynes/cm². Typically, the surface tension will be in the range from about 15 dynes/cm² to about 30 dynes/cm², more typically from about 18 dynes/cm² to about 28 dynes/cm², and most generally from about 20 dynes/cm² to about 25 dynes/cm².

The weight ratio of the highly arylated polysiloxane fluid to the spreading agent will, in general, be from about 1000:1 to about 1:1, preferably from about 100:1 to about 2:1, more preferably from about 50:1 to about 2:1, most preferably from about 25:1 to about 2:1. When fluorinated surfactants are used, particularly high polysiloxane fluid to spreading agent ratios may be effective due to the efficiency of these surfactants. Thus, it is contemplated that ratios significantly above 1000:1 may be used.

Silicone fluids suitable for use in the compositions of the present invention are disclosed in U.S. Pat. No. 2,826,551, U.S. Pat. No. 3,964,500, U.S. Pat. No. 10 4,364,837, British Pat. No. 849,433, and *Silicon Compounds*, Petrarch Systems, Inc. (1984), all of which are incorporated herein by reference.

e. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin. As is apparent to one of ordinary skill in the art, the degree of cross-linking that is required in order to result in a silicone resin will vary according to the specific silane units incorporated into the silicone resin. Generally, silicone materials which have a sufficient level of trifunctional and tetrafunctional siloxane monomer units (and hence, a sufficient level of cross-linking) such that they dry down to a rigid, or hard, film are considered to be silicone resins. The ratio of oxygen atoms to silicon atoms is indicative of the level of cross-linking in a particular silicone material. Silicone resins suitable for use in the compositions of the present invention generally have at least about 1.1 oxygen atoms per silicon atom. Preferably, the ratio of oxygen to silicon atoms is at least about 1.2:1.0. Silanes used in the manufacture of silicone resins include, but are not limited to: monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are available from General Electric as GE SS4230 and GE SS4267. Commercially available silicone resins are generally supplied in a dissolved form in a low viscosity volatile or non-volatile silicone fluid. The silicone resins for use herein should be supplied and incorporated into the present compositions in such dissolved form, as will be readily apparent to one of ordinary skill in the art.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence. Typical alternate substituents include, but are not limited to, groups such as vinyl, phenyls, amines, hydroxyls, and the like. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin indicates higher levels of cross-linking. As discussed above, however, the overall level of cross-linking can also be indicated by the oxygen to silicon ratio.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described herein).

It is believed that these organic conditioning oils provide the shampoo composition with improved conditioning performance when used in combination with the essential components of the composition, and in particular when used in combination with cationic polymers (described herein). The conditioning oils may add shine and luster to the hair. Additionally, they may enhance dry combing and dry hair feel. Most or all of these organic conditioning oils are believed to be solubilized in the surfactant micelles of the shampoo composition. It is also believed that this solubilization into the surfactant micelles contributes to the improved hair conditioning performance of the compositions herein.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b. Polyolefins

Organic conditioning oils for use in the compositions of the present invention can also include liquid polyolefins, more preferably liquid poly-α-olefins, most preferably hydrogenated liquid, poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid, hexanoic acid, heptanoic acid, and octanoic acid). Specific non-limiting examples of di- and tri- alkyl and alkenyl esters of carboxylic acids include isocetyl stearoyl stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, most preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

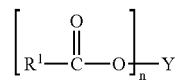

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

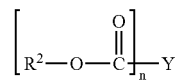

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

It is believed that the preferred synthetic esters provide improved wet hair feel when used in combination with the essential components of the compositions of the present invention, particularly when used in combination with the cationic polymer component (described herein). These synthetic esters improve wet hair feel by reducing the slimy or excessively conditioned feel of wet hair that has been conditioned by a cationic polymer.

Specific non-limiting examples of suitable synthetic fatty esters for use in the compositions of the present invention include: P-43 ($C_8$–$C_{10}$ triester of trimethylolpropane), MCP-684 (tetraester of 3,3 diethanol-1,5 pentadiol), MCP 121 ($C_8$–$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Some other preferred silicone conditioning agents for use in the compositions of the present invention include: Abil® S 201 (dimethicone/sodium PG-propyidimethicone thiosulfate copolymer), available from Goldschmidt; DC Q2-8220 (trimethylsilyl amodimethicone) available from Dow Corning; DC 949 (amodimethicone, cetrimonium chloride, and Trideceth-12), available from Dow Corning; DC 749 (cyclomethicone and trimethylsiloxysilicate), available from Dow Corning; DC2502 (cetyl dimethicone), available from Dow Corning; BC97/004 and BC 99/088 (amino functionalized silicone microemulsions), available from Basildon Chemicals; GE SME253 and SM2115-D2_and SM2658 and SF1708 (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

Anti-Dandruff Actives

The compositions of the present invention may also contain an anti-dandruff agent. Suitable, non-limiting examples of anti-dandruff particulates include: pyridinethione salts, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, most preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), most preferably 1-hydroxy-2-pyridinethione salts in platelet particle form, wherein the particles have an average size of up to about 20µ, preferably up to about 5µ, most preferably up to about 2.5µ. Salts formed from other cations, such as sodium, may also be suitable. Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, all of which are incorporated herein by reference. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

2. Selenium Sulfide

Selenium sulfide is a particulate anti-dandruff agent suitable for use in the compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein $x+y=8$. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107, all of which descriptions are incorporated herein by reference.

3. Sulfur

Sulfur may also be used as a particulate anti-dandruff agent in the compositions of the present invention. Effective concentrations of the particulate sulfur are typically from about 1% to about 4%, by weight of the composition, preferably from about 2% to about 4%.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR™ and SUPEROL™ available from The Procter & Gamble Company, CRODEROL GA7000™ available from Croda Universal Ltd., PRECERIN™ series available from Unichema, and a same tradename as the chemical name available from NOF; propylene glycol with tradename LEXOL PG-865/855™ available from Inolex, 1,2-PROPYLENE GLYCOL USP available from BASF; sorbitol with tradenames LIPONIC™ series available from Lipo, SORBO™, ALEX™, A-625™, and A-641™ available from ICI, and UNISWEET 70™, UNISWEET CONC™ available from UPI; dipropylene glycol with the same tradename available from BASF; diglycerin with tradename DIGLYCEROL™ available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from lchimaru Pharcos; sodium adenosine phosphate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Suspending Agent

The compositions of the present invention may further comprise a suspending agent at concentrations effective for suspending water-insoluble materials in dispersed form in the compositions or for modifying the viscosity of the composition. Such concentrations range from about 0.1% to about 10%, preferably from about 0.3% to about 5.0%, by weight of the compositions.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyalkylene glycols having a molecular weight of more than about 1000 are useful herein. Useful are those having the following general formula:

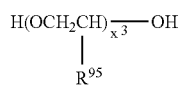

wherein $R^{95}$ is selected from the group consisting of H, methyl, and mixtures thereof. When $R^{95}$ is H, these materials are polymers of ethylene oxide, which are also known as polyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist. In the above structure, x3 has an average value of from about 1500 to about 25,000, preferably from about 2500 to about 20,000, and more preferably from about 3500 to about 15,000. Other useful polymers include the polypropylene glycols and mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300, 000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9-M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents. Other long chain acyl derivatives suitable for use as suspending agents include N,N-dihydrocarbyl amido benzoic acid and soluble salts thereof (e.g., Na, K), particularly N,N-di(hydrogenated) C.sub.16, C.sub.18 and tallow amido benzoic acid species of this family, which are commercially available from Stepan Company (Northfield, Ill., USA).

Examples of suitable long chain amine oxides for use as suspending agents include alkyl (C.sub.16 –C.sub.22) dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino is acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thioindigoid, quinacridone, phthalocianine, botanical, natural colors, including: water soluble components such as those having C. I. Names: Acid Red 18, 26, 27,33, 51, 52, 87, 88, 92, 94, 95, Acid Yellow 1, 3, 11, 23, 36, 40, 73, Food Yellow 3, Food Green 3, Food blue 2, Food Red 1, 6, Acid Blue 5, 9, 74, Pigment Red 57-1, 53(Na), Basic Violet 10, Solvent Red 49, Acid orange 7, 20, 24, Acid Green 1, 3, 5, 25, Solvent Green 7, Acid Violet 9, 43; water insoluble components such as those having C. I. Names: Pigment Red 53(Ba), 49(Na), 49(Ca), 49(Ba), 49(Sr), 57, Solvent Red 23, 24, 43, 48, 72, 73, Solvent Orange 2, 7, Pigment Red 4, 24, 48, 63(Ca)3, 64, Vat Red 1, Vat blue 1, 6, Pigment Orange 1, 5, 13, Solvent Yellow 5, 6, 33, Pigment Yellow 1, 12, Solvent Green 3, Solvent Violet 13, Solvent Blue 63, Pigment Blue 15, titanium dioxides, chlorophyllin copper complex, ultramarines, aluminum powder, bentonite, calcium carbonate, barium sulfate, bismuthine, calcium sulfate, carbon black, bone black, chromic acid, cobalt blue, gold, ferric oxides, hydrated ferric oxide, ferric ferrocyanide, magnesium carbonate, manganous phosphate, silver, and zinc oxides.

The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

The compositions of the present invention may also contain chelating agents such as: 2,2'-dipyridylamine; 1,10-phenanthroline {o-phenanthroline}; di-2-pyridyl ketone; 2,3-bis(2-pyridyl)pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'-dipyridyl; 2,2'-biquinoline; di-2-pyridyl glyoxal {2,2'-pyridil}; 2-(2-pyridyl)benzimidazole; 2,2'-bipyrazine; 3-(2-pyridyl)-5,6-diphenyl-1,2,4-triazine; 3-(4-phenyl-2-pyridyl)-5-phenyl-1,2,4-triazine; 3-(4-phenyl-2-pyridyl)-5,6-diphenyl-1,2,4-triazine; 2,3,5,6-tetrakis-(2'-pyridyl)-pyrazine; 2,6-pyridinedi-carboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol {lumazine}; 2,2'-dipyridyl; and 2,3-dihydroxypyridine.

Other embodiments

In another embodiment, the compositions of the present invention can be in the form of creams, sprays, lotions, gels, and the like. Preferably the cosmetic compositions herein are in the form of an oil-in-water emulsion of one or more oil phases in an aqueous continuous phase, each oil phase comprising a single oily component or a mixture of oily components in miscible or homogeneous form but said different oil phases containing different materials or combinations of materials from each other. The overall level of oil phase components in the compositions of the invention is preferably from about 0.1% to about 60%, preferably from about 1% to about 30% and more preferably from about 1% to about 10% by weight.

A wide variety of optional ingredients such as non-occlusive moisturizers, humectants, gelling agents, neutralizing agents, perfumes, colouring agents and surfactants, can be added to the skin compositions herein.

In personal-care products it may be highly preferred to include cationic organic compounds, such as cationic surfactants. It can be preferred that the compositions comprise one or more other ingredient which can reduce dermatitis or compounds which can help the healing of the skin, such as triacetin, benzalkonium salts, metal-containing compounds, in particular zinc-containing compounds, vitamins and cortisone's, and also compounds to soften the skin such as vaseline, glycerin, triethyleneglycol, lanolin, paraffin and another group of polymers extensively employed by pharmaceutical and cosmetic manufactures, as also described herein.

In deodorant and/or antiperspirant compositions it may be highly preferred that a perfume is present, preferably combined with additional perfume longevity increasing aids or residuality improving aids, including di-octyl adipate and/or Farnisol. Also highly preferred are triclosan, zinc phenol sulphonate, propylene glygol and/or dipropylene glycol. Useful may also be aluminium compounds such as aluminium chloride, aluminium chlorohydrate and including zirconium and/or zirconium aluminium glycinate, or mixtures thereof. These ingredients may be present at any suitable level, preferably being from 0.01% to about 10%, preferably 0.05% to 5% or more preferably from 0.05% to 3% or even to 2% or even to 5% by weight of the deodorant composition.

What is claimed is:

1. A composition for treating dandruff comprising:
   (a) surfactant; and
   (b) fospirate.

2. The composition of claim 1 further comprising an anti-dandruff agent.

3. The composition of claim 1 wherein said surfactant is a detersive surfactant.

4. A composition for treating dandruff comprising:
   (a) surfactant; and
   (b) 1,6-bis-(cyclohexyloximinocarbonylamino)-hexane.

5. The composition of claim 5 further comprising an anti-dandruff agent.

6. The composition of claim 5 wherein said surfactant is a detersive surfactant.

7. A method to inhibit the activity of any *Malassezia globosa* lipase, comprising applying the composition of claim 1 to skin.

8. A method to inhibit the activity of any *Malassezia globosa* lipase, comprising applying the composition of claim 4 to skin.

* * * * *